United States Patent [19]

Donzis

[11] Patent Number: 5,397,773
[45] Date of Patent: Mar. 14, 1995

[54] PHOTOPROTECTIVE COMPOSITION CONTAINING YEAST EXTRACT

[76] Inventor: Byron A. Donzis, 3008 Rodgerdale Rd., Houston, Tex. 77042

[21] Appl. No.: 31,758

[22] Filed: Mar. 15, 1993

Related U.S. Application Data

[63] Continuation-in-part of Ser. No. 435,032, Nov. 9, 1989, Pat. No. 5,223,491.

[51] Int. Cl.$^6$ .............................................. A61K 35/72
[52] U.S. Cl. .................................. 514/54; 424/195.1; 424/520
[58] Field of Search ............... 514/54; 424/195.1, 520, 424/93 R, 93 S, 59

[56] References Cited

PUBLICATIONS

Elmets et al., Photodermatol. Photoimmunol. Photomed 9(3):113–120 (1992). Abstract BA 96:8624.
Daniels et al., J. Invest. Dermatol., (1961) 37:351–357.
Gilchrest et al., J. Am. Acad. Dermatol., (1981) 5:411–422.
Koh et al., Photochemistry and Photobiology, (1990) 51:765–779.
Krutman et al., Photochemistry and Photobiology, (1988) 48:787–798.
Toews et al., J. Immuno., (1980) 124:445–453.
Rae et al., J. Dermatol. Surg. Oncol., (1989) 15:1199–1202.
Kiistala et al., J. Investigative Dermatol., (1967) 48:466–477.
Elmets et al., J. Investigative Dermatol., (1982) 79:340–345.
Elmets, In: "Pharmacology of the Skin," Mukhtar, ec., CRC Press, 1992, pp. 389–416.

Primary Examiner—Douglas W. Robinson
Assistant Examiner—Jean C. Witz
Attorney, Agent, or Firm—Butler & Binion; Sue Z. Shaper

[57] ABSTRACT

A composition and method for protecting skin from the damaging of UV or solar radiation, comprising topical application to the skin of a composition containing a yeast cell wall extract.

7 Claims, 1 Drawing Sheet

PHOTOPROTECTIVE COMPOSITION CONTAINING YEAST EXTRACT

This is a continuation-in-part of U.S. patent application Ser. No. 435,032, filed Nov. 9, 1989, now U.S. Pat. No. 5,223,491, which is hereby incorporated by reference for all purposes.

FIELD OF THE INVENTION

This invention relates to method for protecting against the damaging effects of ultraviolet light in the skin. More particularly, this invention relates to use of a cosmetic composition containing a yeast polyglucan in a method of protecting skin from the damaging effects of the sun.

BACKGROUND OF THE INVENTION

It is well known that exposure of skin to solar or ultraviolet (UV) radiation mediates a number of harmful effects in the human body. Acute UV exposure causes solar erythema or sunburn and is associated with the development of dyskeratotic cells within the epidermis (sunburn cells), a parameter that may reflect UV-induced DNA damage. Chronic UV exposure is also well recognized as an etiological agent for cutaneous squamous cell and basal cell carcinoma and may play a role in promoting the development of malignant melanoma. More recently, studies have indicated that UV radiation can profoundly influence the immune response. In particular, UV radiation has an inhibitory effect on epidermal Langerhans cells.

For these reasons, it is highly desirable to provide photoprotective methods to protect human skin from the above-described damaging effects of solar or UV radiation. It is further desirable to provide topical cosmetic products in which effective photoprotective agents have been incorporated.

SUMMARY OF THE INVENTION

The present invention provides a novel photoprotective method for protecting skin from the damaging effects of solar or UV radiation. The photoprotective method of the present invention a composition containing a yeast extract, preferably an insoluble yeast extract comprised of polyglucan, and most preferably comprised of beta glucan having predominantly beta 1—glycosidic linkages is used. In the method of the present invention, yeast glucan is incorporated into a composition for topical application to the skin where it exerts its protective effects. The photoprotective yeast extract of the present invention may be combined with cosmetic products, or with traditional sunscreen products.

DETAILED DESCRIPTION OF THE PREFERRED EMBODIMENT

Figure 1:
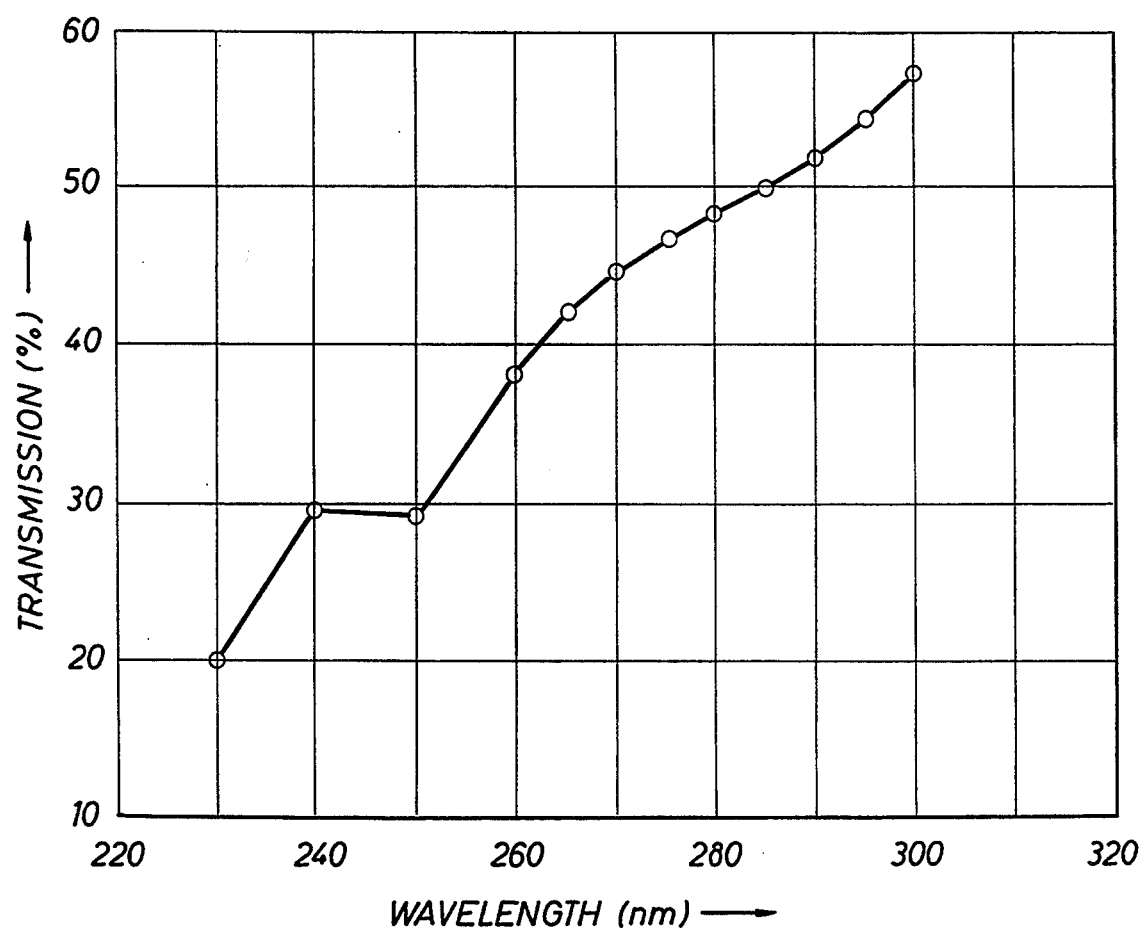
FIGURE 1 is a graph depicting the effect of a yeast cell wall extract on the transmission of light.

Yeast Extract.

Yeast cells may be sonicated or otherwise broken to prepare a yeast cell wall material prior to extraction. Preferred yeast is that of the genus Saccharomyces and most preferably is *Saccharomyces cerevisiae*, including Baker's yeast and Brewer's yeast.

Yeast cells or yeast cell walls are extracted by methods known in the art, and preferably are extracted by the methods described in U.S. Ser. No. 435,032 to extract yeast cell wall glucan. Glucan may be prepared by these methods, or may be purchased commercially from Immudyne, Inc. (Palo Alto, Calif.) as insoluble yeast extract (Nayad) or as soluble yeast extract (LCP-100).

Purified yeast cell wall glucan is preferably essentially protein and endotoxin-free, and most preferably is comprised of polyglucose having predominantly beta 1-3 glycosidic linkages.

Photoprotective composition

In its simplest form, the photoprotective method of the present invention includes applying to the skin glucan prepared as a suspension in a carrier suitable for topical application to the skin. Such carriers may be aqueous solutions or suspensions, lotions, creams, or ointments.

Compositions comprising glucan may also contain moisturizers or agents to enhance entry of the compound into the skin, agents to enhance retention of the product on the skin, fragrance, color, and the like. In a preferred embodiment, glucan is added to commercial skin care products such as lip balms, suntan lotions, cosmetics, and the like, to impart photoprotective qualities to these products. The photoprotective composition may also include known sunscreen compounds such as octylmethoxycinnamate or benzophenone, and may optionally contain cholesterol such as 7-dehydrocholestrol.

By way of example, a photoprotective lotion comprising the glucan product may be comprised of the following: glucan, water, propylene glycol, avocado oil, isocetyl stearate, octylmethoxy cinnamate, polysorbate 60, maleated soybean oil, stearic acid, silicone fluid, cetyl acetate, vitamin E acetate, glycerol monostearate, propylene glycol monostearate, sorbitan stearate, vitamin A palmitate, benzophenone-3, silicone wax, triethanolamine, diazolidinylurea, methylparaben, lanolin alcohol, disodium edetate, carbomer 934, and propylparaben.

The photoprotective method of the present invention utilizes a composition which preferably contains yeast cell wall glucan in an amount ranging from approximately 0.01 to 20 mg/oz., and more preferably from approximately 0.01 to 1 mg/oz. In the method of the present invention a composition containing yeast cell wall glucan is topically applied to the skin prior to exposure to solar or UV radiation. Pretreatment of the skin with the photoprotective yeast glucan composition is effective to reduce UV-induced erythema (sunburn), to prohibit the production of sunburn cells, and to protect Langerhans cells against adverse effects of UV radiation.

EXAMPLES

The invention may be better understood by reference to the following examples:

EXAMPLE 1

PREPARATION OF YEAST EXTRACT

Dried Baker's yeast (500 grams) was added to 2.4 liters of warm (50 to 60° C.), 1.5N sodium hydroxide while stirring. The mixture was stirred until the yeast was thoroughly dispensed. The mixture was then autoclaved for thirty minutes at approximately 15 psi. After cooling to room temperature, the mixture was centrifuged at 5000×G for 15 minutes. The supernatant was removed and the pellets were resuspended with vigorous stirring in a total of one liter of distilled water. The water mixture was centrifuged at 5000×G for 15 minutes and a supernatant was removed. This water-wash was repeated two times for a total of three water-washes.

The washed pellet was resuspended in two liters of 3% glacial acetic acid and heated at 85° C. for one hour. The acid mixture was then centrifuged as described above and the supernatant removed. The pellet was washed with a total one liter of distilled water, as described above. The supernatant was removed and the pellets were resuspended in a total of one liter of absolute ethanol. The residue was again centrifuged as described above. The ethanol wash was repeated one time for a total of two ethanol washes and the pellet then resuspended in 0.5 liters of absolute ethanol. The ethanol mixture was filtered on a glass fiber filter in a Buchner funnel pressing out the residual ethanol. The filtered cake produced from the Buchner funnel was spread out on a large glass dish and air dried from four to five hours, periodically breaking up any lumps. The precipitate was dried at 40° C. under a vacuum while continuing to breakup any lumps. This material was dried at 40° C. under a vacuum for approximately 24 hours or until a constant weight was reached. The yield of this extraction material was approximately 50 grams.

EXAMPLE 2

USE OF TOPICAL YEAST GLUCAN COMPOSITION AS A PHOTOPROTECTIVE AGENT

The yeast glucan prepared in Example 1 was utilized in studies to examine its photoprotective effects on human skin. One milligram of the yeast glucan was added per ounce of oil-in-water emulsion (O/W) carrier.

Healthy adults, aged 18 to 40 having sun-reactive skin types of II or III were instructed to apply the various test preparations in a manner simulating normal consumer usage.

The study protocol included the following groups:
1. Untreated Control
2. Untreated, UV Irradiated Skin
3. Oil and Water Emulsion (O/W)
4. 7-dehydrocholesterol (DHC) in O/W
5. DHC and two commercial sunscreens, 7.5% octylmethoxcinnamate and 3% benzophenone (SS) in O/W
6. DHC and yeast cell wall glucan (G) in O/W
7. DHC, G, and SS in O/W Test areas of skin, 5×5 centimeter areas on the inner aspect of each forearm, were treated daily for two weeks with the appropriate test preparation. The pretreated areas as well as adjacent areas of skin (control) were exposed to a UVB dose equivalent of 1.5 times the minimal erythema dose (MED) each day for four consecutive days. Treatment with the topical preparations was continued through the four days of UV irradiation. The agents were applied fifteen to thirty minutes before UV exposure. (MED was calculated by exposing the back of each subject to gradually increasing UV doses. The lowest dose providing uniform erythema over the irradiation site was considered to be the MED.)

The UV radiation source was a bank of four FS72 sunlamps whose emission spectrum lies primarily within the UVB range. Output was monitored with an international light IL700 radiometer coupled to a UVB photodetector.

Specimens of epidermis were obtained by removing the roofs of vacuum-induced blisters as described in Kustala et al., *J. Invest. Dermatol.*, 48:466-477, 1967, from the UV-treated sites and, from control, untreated sites. Blisters were raised from each treatment site on one arm immediately after UV exposure and from the other arm one week after UV exposure.

HLA-DR-positive and CD1a-positive cells were identified by staining portions of each blister en face for immunofluorescence using anti-HLA-DR (Becton-Dickinson, Sunnyvale, Calif.) and anti-CD1a (OKT6, Ortho Pharmaceutical, Riritan, N.J.) monoclonal antibodies, following the procedure described in Elmets et al. *J. Invest. Dermatol.*, 79:340-345, 1982. Sunburn cells were identified in 4-$\mu$m formalin-fixed sections of epidermis that were stained for routine histology with hematoxylin and eosin.

HLA-DR-positive and CD1a-positive Langerhans cells were quantified in en face specimens of epidermis by determining the mean number of Langerhans cells per $mm^2$. Five high-power (times 400) microscope fields were examined using a Nikkon immunofluorescence microscope equipped with epi-fluorescence. All specimens were examined in a blinded fashion. The presence of positively stained cell bodies was used as the criterion by which cells were counted. Preliminary studies were conducted in which the effect of the vehicle alone without UV irradiation was assessed. No difference between HLA-DR-positive and CD1a-positive Langerhans cells in vehicle treated skin and in untreated skin was observed (data not shown).

The mean number of sunburn cells per linear mm of epidermis was quantified by examining ten high power fields (×400) with an American Optical microscope. The presence of eosinophilic staining cells without nuclei or with dyskeratotic nuclei was used as the criterion for counting sunburn cells. All specimens were read in a blinded manner. Preliminary studies were conducted in which the effect of the vehicle alone without UV irradiation was assessed. No differences between the number of sunburn cells in vehicle-treated skin and in untreated skin were observed (data not shown).

Untreated skin developed mild to marked erythema when exposed to a dose of UVB corresponding to 1.5 MED daily for four consecutive days as scored by visual inspection. Skin pretreated with the oil-in-water emulsion alone or with 7-dehydrocholesterol in the water and oil emulsion produced an erythema response which was identical to that of untreated skin.

Results-Erythema

The preparation containing the yeast extract in the absence of sunscreens afforded partial protection against UV-induced erythema. Mild erythema was observed in the specimens, however, it was clearly less marked than in untreated UV irradiated skin.

Both compositions which included commercially available sunscreens provided complete protection against UVB-induced erythema.

Results-Effect on Langerhans Cells

To assess the effect of the test compositions on Langerhans cell concentrations and morphology, skin specimens were stained with monoclonal antibodies to the HLA-DR and CD1a Langerhans cell phenotypic markers. As shown in Table 1, there was a marked decrease in positively stained cells immediately after completion of the UV irradiation protocol in specimens treated with the oil-in-water emulsion alone or with the oil-in-water emulsion containing 7-dehydrocholesterol. The magnitude of this reduction was identical to that observed in UV-irradiated epidermis which was not treated. The morphology of those positively stained cells remaining in the specimen lacked dendrites and exhibited a markedly atypical morphology.

TABLE 1

| PRETREATMENT | UV EXPOSURE | HLA-DR POSITIVE LANGERHANS CELL CONCENTRATIONS* | CD1a-POSITIVE LANGERHANS CELL CONCENTRATIONS* |
|---|---|---|---|
| NONE | − | 639.2 ± 25.6 | 626.2 ± 14.2 |
| NONE | + | 371.4 ± 30.0 | 263.3 ± 38.3 |
| O/W | + | 341.6 ± 32.2 | 288.2 ± 43.3 |
| DHC | + | 321.7 ± 30.0 | 288.2 ± 40 |

*The data represent the mean concentrations of Langerhans cells per $mm^2$ ± SEM from five specimens In specimens pretreated with the oil-in-water emulsion containing 7-dehydrocholesterol and yeast extract, a partial protection of Langerhans cells against the adverse effects of UV radiation was seen. As shown in Table 2, immediately after UV exposure the number of HLA-DR positive and CD1a positive Langerhans cells significantly decreased in untreated specimens. In specimens pretreated with the composition containing the yeast extract alone, the decrease in Langerhans cells was attenuated. Greater attenuation was seen by those compositions containing sunscreens alone with the best protection afforded by the composition containing both commercially available sunscreens and the yeast extract.

TABLE 2

| PRETREATMENT | UV EXPOSURE | HLA-DR POSITIVE LANGERHANS CELL CONCENTRATIONS* | CD1a-POSITIVE LANGERHANS CELL CONCENTRATIONS* |
|---|---|---|---|
| NONE | − | 746.5 ± 56.8 | 766.6 ± 52.7 |
| NONE | + | 321.3 ± 89.9 | 173.7 ± 92.7 |
| YEAST EXTRACT | + | 477.9 ± 69.8 | 423.5 ± 93.2 |
| SUNSCREENS | + | 695.9 ± 70.4 | 707.9 ± 70.8 |
| SUNSCREENS PLUS YEAST EXTRACT** | + | 747.8 ± 77.0 | 733.1 ± 87.5 |

*The data represent the mean concentrations of Langerhans cells per $mm^2$ ± SEM from ten specimens.
**The data represent the mean concentration of Langerhans cells per $mm^2$ ± SEM from nine specimens.

As shown in Table 3, the photoprotective effect of the yeast extract on the Langerhans cell population was still evident at one week past treatment. These findings suggest that the yeast extract accelerated the return of the epidermis to a more normal histological appearance after UV exposure.

TABLE 3

| PRETREATMENT | UV EXPOSURE | HLA-DR POSITIVE LANGERHANS CELL CONCENTRATIONS* | CD1a-POSITIVE LANGERHANS CELL CONCENTRATIONS* |
|---|---|---|---|
| NONE | − | 746.3 ± 54.3 | 705.4 ± 79.3 |
| NONE | + | 465.9 ± 73.8 | 388.6 ± 99.1 |
| YEAST EXTRACT | + | 560.8 ± 73.8 | 538.0 ± 57.8 |

*The data represent the mean concentrations of Langerhans cells per $mm^2$ ± SEM from ten specimens.

Results - Sunburn Cell Formation

The photoprotective preparations were also evaluated for their capacity to protect against sunburn cell formation. As shown in Table 4, the mean number of dyskeratotic cells per linear mm of skin increased significantly with exposure to radiation. Pretreatment of skin with the oil-in-water emulsion had no effect on the number of sunburn cells observed. Addition of 7-dihydroxycholesterol to the oil-in-water emulsion, however, resulted in a moderate decrease in the number of sunburn cells per linear mm. As shown in Table 5, pretreatment of skin with the preparation containing yeast extract produced a 62% decrease in sunburn cell formation. The two preparations containing commercial sunscreens completely prevented the UV radiation-induced production of sunburn cells.

TABLE 4

| PRETREATMENT | UV EXPOSURE | TIME AFTER UV EXPOSURE | NUMBER OF SUNBURN CELLS* |
|---|---|---|---|
| NONE | − | − | 1.0 ± 0.3 (6) |
| NONE | + | IMMEDIATE | 36.4 ± 1.3 (5) |
| O/W | + | IMMEDIATE | 38.0 ± 1.5 (4) |
| DHC | + | IMMEDIATE | 23.8 ± 4.3 (4) |
| O/W | + | DAY 7 | 5.4 ± 2.0 (5) |

TABLE 4-continued

| PRETREATMENT | UV EXPOSURE | TIME AFTER UV EXPOSURE | NUMBER OF SUNBURN CELLS* |
|---|---|---|---|
| DHC | — | DAY 7 | 5.8 ± 2.1 (5) |

*The data represent the mean concentrations of sunburn cells per linear mm$^2$ ± SEM. The number of specimens is given in parenthesis.

TABLE 5

| PRETREATMENT | UV EXPOSURE | SUNBURN CELLS IMMEDIATELY AFTER UV EXPOSURE$^a$ | SUNBURN CELLS ONE WEEK AFTER UV EXPOSURE$^b$ |
|---|---|---|---|
| NONE | — | 1.5 ± 0.4 | 1.2 ± 0.2 |
| NONE | + | 33.4 ± 6.4 | 14.8 ± 11.2 |
| YEAST EXTRACT | + | 13.6 ± 7.2 | 1.4 ± 0.4 |
| SUNSCREENS | + | 1.8 ± 0.4 | 1.4 ± 0.2 |
| SUNSCREEN PLUS YEAST EXTRACT | + | 1.8 ± 0.4 | 2.0 ± 0.4 |

$^a$The data represent the mean value plus or minus SEM of sunburn cells per linear mm of epidermis from ten specimens, except that in the group treated with UV alone the data is the mean of nine specimens. One specimen contained sunburn cells that were too numerous to count and was therefore excluded from the calculations.

$^b$Data represent the mean plus or minus SEM sunburn cells per linear mm of epidermis from nine specimens for all groups except UV alone. The data in the UV treated group is the mean of seven specimens. Two specimens in the group treated with UV alone contain sunburn cells that were too numerous to count and were therefore excluded from the calculations.

EXAMPLE 3

AQUEOUS SOLUTION OF YEAST EXTRACT AS SUNSCREEN

A commercially available yeast cell wall extract (LCP-100, ImmunoDyne, Palo Alto, Calif.) was prepared as an aqueous solution, 250 μg/ml. The transmission of various wavelengths of ultraviolet light through the solution was measured using a spectrophotometer. As shown in FIGURE 1, sixty-five percent of the energy at 270 nm (wavelength of maximal suppressive activity) was absorbed by LCP-100, indicating that this material is an effective sunscreen.

I claim:

1. A method for protecting skin from the damaging effects of UV radiation comprising:
   applying topically to the skin a composition containing yeast cell wall extract comprising yeast glucan in an amount of between 0.01 and 20mg/oz of the composition.

2. The method of claim 1, said yeast glucan having predominantly beta, 1-3 glycosidic linkages.

3. The method of claim 2, wherein said yeast glucan is in the amount of between 0.02 and 20 mg/ounce of the composition.

4. The method of claim 3, wherein said yeast glucan is in the amount of between 0.01 and 10 mg/ounce of the composition.

5. The method of claim 3, wherein said yeast glucan is in the amount of between 0.01 and 1.0 mg/ounce of the composition.

6. The method of claim 1, wherein the yeast cell wall extract is insoluble in aqueous solution.

7. A method for protecting skin from the damaging effects of UV radiation comprising applying topically to the skin an effective amount of a composition containing yeast cell wall extract comprising yeast glucan and cholesterol.

* * * * *